United States Patent [19]

Avellanet

[11] Patent Number: 5,733,496
[45] Date of Patent: Mar. 31, 1998

[54] ELECTRON BEAM IRRADIATION OF CATHETERS TO ENHANCE STIFFNESS

[75] Inventor: Frank J. Avellanet, Miami, Fla.

[73] Assignee: Cordis Corp., Miami Lakes, Fla.

[21] Appl. No.: 549,117

[22] Filed: Oct. 27, 1995

[51] Int. Cl.⁶ .................................................. B29C 35/08
[52] U.S. Cl. ...................... 264/470; 264/485; 264/167; 264/209.6; 264/236
[58] Field of Search ...................... 264/470, 485, 264/209.6, 236, 495, 488, 167

[56] References Cited

U.S. PATENT DOCUMENTS

| | | | |
|---|---|---|---|
| 3,563,870 | 2/1971 | Tung et al. | 264/470 |
| 3,624,045 | 11/1971 | Stivers | 264/470 |
| 4,134,812 | 1/1979 | Sasaki et al. | 264/485 |
| 4,321,226 | 3/1982 | Markling | 264/149 |
| 4,665,604 | 5/1987 | Dubowik | 264/150 |
| 4,764,324 | 8/1988 | Burnham | 264/151 |
| 4,963,306 | 10/1990 | Weldon | 264/149 |
| 5,059,375 | 10/1991 | Lindsay | 264/173.19 |
| 5,087,394 | 2/1992 | Keith | 264/470 |
| 5,565,523 | 10/1996 | Chen et al. | 525/176 |
| 5,622,665 | 4/1997 | Wang | 264/150 |

FOREIGN PATENT DOCUMENTS

| | | | |
|---|---|---|---|
| 2911777 | 10/1980 | Germany | 264/485 |
| 8003671 | 2/1981 | Netherlands | 264/485 |

*Primary Examiner*—Jeffery R. Thurlow
*Attorney, Agent, or Firm*—Aquilino & Welsh

[57] ABSTRACT

A catheter and method for manufacturing catheters. The method includes the steps of manufacturing a tubular member sized and dimension for use as a catheter and irradiating the tubular member to impart a desired stiffness to the tubular member. A single coat catheter is constructed from a polymer tubular member irradiated to cross-link polymer molecules within the polymer tubular member, wherein cross-linking the polymer molecules alters properties of the polymer molecules to create a polymer tubular member having improved stiffness characteristics.

7 Claims, No Drawings

ELECTRON BEAM IRRADIATION OF CATHETERS TO ENHANCE STIFFNESS

BACKGROUND OF THE INVENTION

1. Field of the Invention

The invention relates to catheters. More specifically, the invention relates to polymer tubular members used as catheters, wherein the tubular members have been irradiated by an electron beam to enhance the stiffness of the tubular members.

2. Description of the Prior Art

Catheters are commonly used in medical procedures where materials must be transported to positions within the vascular system of a human being. Often times, the catheter must be transported through a tortuous path before the distal end of the catheter reaches the predetermined location within the vascular system. Consequently, an ideal catheter combines a maximum inside diameter, permitting transport of materials within the catheter body, with a minimum outside diameter, permitting the catheter to move easily through the tortuous vascular system. The combination of these requirements, however, often results in a tube having a very thin and weak wall.

More specifically, a catheter must be flexible enough to navigate through tortuous paths and yet have substantial rigidity to allow a physician to torque it and push it in such a way that he or she can reach a desired location inside the body without kinking or damaging the arteries. Physicians refer to these features as torqueability and pushability, respectively.

Prior to the present invention, it was not possible to manufacture a single coat of extruded polymer tubing having the stiffness characteristics required in an effective catheter. Attempts have, therefore, been made to enhance the stiffness characteristics of extruded tubing so that it may effectively be used as a catheter. Generally, these methods result in multicoat tubular members, wherein the additional coats provide the stiffness not provided by the central extruded tubular member. One method previously employed is the application of braided wire to the exterior of extruded polymer tubing. Braided extruded tubing includes a central extruded polymer tube having a wire braid applied to the outer surface thereof. A top coat, preferably, a biocompatible polymer, is then applied about the central extruded polymer.

While braided extruded tubing provides desirable stiffness characteristics, the tubing does exhibit problems. Specifically, the required manufacturing process is elaborate, labor intensive, time consuming and expensive. For example, the manufacturing process involves sensitive grinding operations. These grinding operations often result in the removal of the top coat of the braided extruded tubing, thereby exposing the braiding. Exposure of the braiding by the removal of the top coat results in tubing which may not be used as catheters.

Additionally, concentricity is required between the central polymer tube, the braiding and the top coat of braided extruded tubing used in catheters. The length and speed at which braided extruded tubing is manufactured often makes the required concentricity difficult to maintain, resulting in eccentrically formed tubing. As with braided extruded tubing having exposed braiding, tubing which is not concentric is unusable in catheters. Waste resulting from improper grinding and eccentric tubing generates substantial undesirable expenses. In view of the prior art techniques for manufacturing catheters, it is apparent that a need continues to exist for a cost effective, reliable, and convenient method for manufacturing catheters having appropriate stiffness characteristics. The present invention provides such a method and a catheter manufactured in accordance with this method.

SUMMARY OF THE INVENTION

It is, therefore, an object of the present invention to provide a method for manufacturing catheters. The method includes the steps of manufacturing a tubular member sized and dimensioned for use as a catheter and irradiating the tubular member with an electron beam to impart a desired stiffness to the tubular member.

It is also an object of the present invention to provide a catheter having enhanced stiffness characteristics. The catheter is constructed from a tubular member sized and dimensioned for use as a catheter, wherein the tubular member is irradiated with an electron beam to impart a desired stiffness to the tubular member.

It is further an object of the present invention to provide a single coat catheter. The single coat catheter is constructed from a polymer tubular member irradiated with an electron beam to cross-link polymer molecules within the polymer tubular member, wherein cross-linking the polymer molecules alters properties of the polymer molecules to create a polymer tubular member having improved stiffness characteristics.

Another object of the present invention is to provide a catheter and method for manufacture, wherein the catheter is manufactured from a polymer material selected from the group consisting of polyamide block copolymers, polyester ether amides, polyetheramides, copolyesters, polyurethanes, polyesters, polyethers, PET (polyethylene terathalate), PTFE (polytetraflouroethylene), PVC (polyvinyl chloride), polyolefins, and blends thereof.

It is also an object of the present invention to provide a catheter having varied stiffness along the longitudinal axis of the catheter. This is achieved by irradiating a tubular member differently along its longitudinal axis to impart varied stiffness along its longitudinal axis. Alternately, varied stiffness may be provide by varying the material composition of a tubular member to impart varied stiffness along the longitudinal axis of the tubular member.

Other objects and advantages of the present invention will become apparent from the following detailed description when viewed in conjunction with the accompanying drawings, which set forth certain embodiments of the invention.

DESCRIPTION OF THE PREFERRED EMBODIMENTS

The detailed embodiments of the present invention are disclosed herein. It should be understood, however, that the disclosed embodiments are merely exemplary of the invention, which may be embodied in various forms. Therefore, the details disclosed herein are not to be interpreted as limited, but merely as the basis for the claims and as a basis for teaching one skilled in the art how to make and/or use the invention.

A catheter in accordance with the present invention is manufactured by irradiating a polymer tubular member with an electron beam to cross-link the polymer molecules and impart a desired stiffness to the tubular member. Specifically, a polymer tubular member is manufactured by conventional extrusion techniques. The polymer tubular member is sized and dimensioned for use as a catheter. It should be understood that the polymer tubular member could be manufactured by techniques other than extrusion, without departing from the spirit of the present invention.

As stated above, the tubular member is preferably manufactured from a polymer material. A wide variety of polymers may be used in accordance with the present invention. Among the materials which may be used are polyamide block copolymers, such as polyester ether amides which are sold under the tradenames PEBAX, VESAMIDE, and GRILON by Atochem, Huels, and Emser, respectively, and polyetheramides which are sold under the tradename GRILON ELY60 by Emser. Further, copolyesters, such as HYTRELL, which is manufactured by DuPont, can be used in accordance with the present invention. Additionally, polyurethanes, such as polyester and polyether type polyurethanes, PET (polyethylene terathalate), PTFE (polytetraflouroethylene), PVC (polyvinyl chloride), polyolefins, and blends of various polymers may be used in accordance with the present invention. It should be understood that the materials discussed above are merely exemplary of polymers that may be used in accordance with the present invention, and a wide variety of materials could be used without departing from the spirit of the present invention.

Once the tubular member is manufactured, it is irradiated with an electron beam. The electron beam causes cross-linking of the polymer molecules, which imparts desirable stiffness characteristics to the tubular member. Generally, when polymer materials are cross-linked, the heat resistance, tensile strength, tensile elongation, and stiffness of the materials exposed to the cross-linking irradiation are improved.

Specifically, polymer molecules and thermoplastic materials, such as polyurethane and nylon, are held together by electrostatic forces. When these materials are heated, the electrostatic forces diminish, the plastic softens and ultimately the plastic flows until it becomes a liquid. Cross-linking through irradiation links the molecules and thereby significantly reduces the material's ability to flow. The "locking" of molecules together by cross-linking also reduces the melt index of the material. In essence, cross-linking of the polymer molecules converts a thermoplastic into a thermoset.

As previously stated, an electron beam is used in accordance with the present invention to cross-link the polymer molecules making up the tubular member. Electron beam accelerators are preferably used to cross-link the molecules. Generally, an electron beam accelerator can be thought of as a high-powered television set. The only difference being that a television set provides a screen which is struck by the electron beam and the electron beam accelerator focuses the electron beam to sweep over a specific target, such as a tubular member to be used as a catheter. The beam of negatively charged electrons penetrates the material, thus altering the properties of the polymer tubular member. In accordance with the present invention, an IMPELA electron beam accelerator, supplied by E-BEAM SERVICES, INC., has been used to cross-link the tubular members, although other electron beam accelerators could be used without departing from the spirit of the present invention.

The electron penetration into the irradiated material, i.e., the tubular member, depends mostly on the energy of the striking electron and the density of the material the electrons are striking. The ability of the electron beam to alter the physical properties of the material, by causing the cross-linking of the molecules, is related to the specific physical shape and properties of the material. With this in mind, the material construction of the tubular member must be considered when determining the application of the electron beam. The specific application of the electron beam is, therefore, dictated by the material construction of the tubular member and the desired stiffness characteristics.

The tubular member can be irradiated in a variety of manners to provide a catheter having varied stiffness along its longitudinal axis. For example, the tubular member can be made from the same polymer along its entire longitudinal axis, and subsequently irradiated differently along its longitudinal axis. This results in a catheter having different stiffness characteristics along its longitudinal axis. Similarly, the tubular member can be manufactured with varying polymer characteristics along its longitudinal axis. This tubular member can then be irradiated consistently along its longitudinal axis to produce a catheter having varied stiffness along its longitudinal axis.

In summary, the net effect that electron beam irradiation can have on a specific material, i.e., how much cross-linking can be achieved, depends on the penetration of the striking electron beam and the density of the material. The amount of energy deposited per unit mass of material is called the absorbed dose, which is one kilojoule of energy deposited per kilogram of material or one kilogray (kGy). When manufacturing catheters in accordance with the present invention, we have found that appropriate dosages of the electron beam can be anywhere from about 1 to 100 kGy. More specifically, it has been found that the application of about 1 to 5 kGy to PEBAX and HYTRELL produces desirable results.

The present method permits the production of a single coat catheter having desirable thickness, diameter and stiffness characteristics. The ability to manufacture a useful single coat catheter obviates the need for multi-coat catheter bodies (as required in the manufacture of braided catheters) and the problems associated with their manufacture.

While the preferred embodiments have been shown and described, it will be understood that there is no intent to limit the invention by such disclosure, but rather, is intended to cover all modifications and alternate constructions falling within the spirit and scope of the invention as defined in the appended claims.

I claim:

1. A method for manufacturing catheters, comprising the following steps:

manufacturing a tubular member sized and dimensioned for use as a catheter, wherein the tubular member is constructed from a polymer material;

irradiating the tubular member by exposing the tubular member to an electron beam dosage of about 1 to 100 kGy to impart a desired stiffness to the tubular member.

2. The method according to claim 1, wherein the tubular member is constructed from a polyester ether amide and is exposed to an electron beam dosage of about 1 to 5 kGy.

3. The method according to claim 1, wherein the polymer material is selected from the group consisting of polyamide block copolymers, polyester ether amides, polyetheramides, copolyesters, polyurethanes, polyesters, polyethers, PET, PTFE, PVC, polyolefins, and blends thereof.

4. The method according to claim 1, wherein the tubular member is constructed from a copolyester and is exposed to an electron beam dosage of about 1 to 5 kGy.

5. The method according to claim 1, wherein the tubular member is manufactured by extrusion.

6. The method according to claim 1, wherein the tubular member has a longitudinal axis and the step of irradiating includes irradiating the tubular member differently along the longitudinal axis of the tubular member to impart varied stiffness along the longitudinal axis of the tubular member.

7. The method according to claim 1, wherein the tubular member has a longitudinal axis and the step of manufacturing includes varying the material composition of the tubular member to impart varied stiffness along the longitudinal axis of the tubular member.

* * * * *